United States Patent [19]

Bauer et al.

[11] Patent Number: 5,424,287
[45] Date of Patent: Jun. 13, 1995

[54] EXTRACT OF BACTERIAL MACROMOLECULES, A PROCESS FOR ITS PREPARATION AND A PHARMACEUTICAL COMPOSITION CONTAINING THE SAME

[75] Inventors: Jacques Bauer, Saint-Sulpice; Pierre Hirt, Preverenges; Adrian Schulthess, Begnins, all of Switzerland

[73] Assignee: Laboratoires OM SA, Meyrin, Switzerland

[21] Appl. No.: 119,124

[22] PCT Filed: Feb. 3, 1993

[86] PCT No.: PCT/CH93/00029
    § 371 Date: Sep. 20, 1993
    § 102(e) Date: Sep. 20, 1993

[87] PCT Pub. No.: WO93/16190
    PCT Pub. Date: Aug. 19, 1993

[30] Foreign Application Priority Data
    Feb. 14, 1992 [CH] Switzerland ............... 450/92

[51] Int. Cl.$^6$ .................. C12P 21/00; A61K 35/74
[52] U.S. Cl. ........................ 514/2; 435/71.1; 435/71.2; 435/71.3; 435/252.1; 435/252.8; 435/253.4; 435/822; 435/849; 435/851; 435/852; 435/871; 435/885; 435/886

[58] Field of Search ............... 435/71.1–71.3, 435/252.1, 253.4, 252.8, 822, 849, 851, 852, 871, 885, 886; 514/2

[56] References Cited

FOREIGN PATENT DOCUMENTS 2396018  1/1979  France .
2405298  5/1979  France .
 633188 11/1982  Switzerland .

*Primary Examiner*—Herbert J. Lilling
*Attorney, Agent, or Firm*—Young & Thompson

[57] ABSTRACT

An extract based on modified bacterial proteins includes a mixture of acid bacterial polyanions having a molecular weight in the range from 10,000 to 1,000,000 and an isoelectric point in the range from 2.5 to 5.5, and in which the added weights of the constituent amino acids amount to at least 50% of the extract. The preparation or this protein extract includes a cultivation of bacteria in an aqueous medium and then the alkaline extraction of this bacterial suspension and the purification of the protein extract. The alkaline extraction is carried out in the presence of a dilute aqueous source of OH$^-$ ions and at a stable pH in the range from 11 to 13, the decrease of this pH during the acid extraction not exceeding 0.4. The protein extract thus obtained can be used as an active ingredient in a pharmaceutical composition.

9 Claims, No Drawings

EXTRACT OF BACTERIAL MACROMOLECULES, A PROCESS FOR ITS PREPARATION AND A PHARMACEUTICAL COMPOSITION CONTAINING THE SAME

FIELD OF THE INVENTION

The present invention is concerned with an extract of bacterial macromolecules and, more particularly, with an extract based on modified bacterial proteins, a process for its preparation and a pharmaceutical composition containing this extract as an active ingredient.

BACKGROUND OF THE INVENTION

Bacterial products are already known which have a therapeutic activity and which are obtained by alkaline hydrolysis. The applicant's patent CH 633 188 discloses for example a concentrate of bacterial lysates having anti-infective properties. The lysates of each bacterial strain are obtained through a progressive alkaline hydrolysis (pH 9-10) which leads to the destruction of the apparent structure of the bacteria.

Actually, the present inventors have established, that bacterial extracts could be obtained having various immunopharmacological properties, such as for example an important immunomodulator activity, by using a different alkaline treatment which makes it possible to retain intact the apparent structure of the treated bacteria. Specifically, this treatment consists in an alkaline extraction using conditions of a high pH and, especially, of a stable pH.

SUMMARY OF INVENTION

Thus, the object of the present invention is on the one hand an extract based on modified bacterial proteins and, on the other hand, a process for the preparation of this protein extract, as they are defined in the claims, respectively.

The invention is also directed at a pharmaceutical composition containing, as the active ingredient, the extract based on bacterial proteins modified according to the invention (designated in the following as "protein extract").

The chemical treatment of bacteria, for example by dilute NaOH, causes deep modifications of the primary, secondary and tertiary structures of bacterial proteins. One can thus note a partial deamidation of asparagine and of glutamine, which is conducive to the formation of aspartic acid and glutamic acid, respectively. Partial racemizations of several amino acids also occur during this process, mainly of aspartic acid, serine and arginine. The overall physicochemical modifications of the structure of the proteins produce polypeptides, the amphionic properties of which are acid. These polypeptides all have low isoelectric points ranging from 2.5 to 5.5, with a higher concentration in the vicinity of 4.5. These structural changes thus produce protein extracts which exhibit immunomodulator properties in vitro and in vivo.

In the protein extract according to the invention, the sum of the constituent amino acids amount to at least 50% (as weight percentage of the lyophilized product), and preferably from 55 to 85% of the protein extract and the lipopolysaccharide content (LPS) is preferably lesser than about $2 \times 10^{-3}\%$. The molecular weight of the constituent elements of the protein extract according to the invention is comprised between 10,000 and 1,000,000. Further, this protein extract includes in its proteinic amino acids, some having a D and an L configuration and a preponderant proportion of acid groups such as those of aspartic acid and glutamic acid. The main amino acids which are racemized are serine with about 25% to 45% of D configuration, aspartic acid with about 10 to 30% and arginine with about 3 to 20%. The use of the term "modified proteins" indicates, amongst others, the presence of amino acids in the D configuration in the protein extract, the L configuration being that of native proteins.

On the other hand, the protein extract according to the invention can include at the most about $10^{-3}\%$ lipopolysaccharides, at the most about 2% free amino acids, at the most about 8% glucides, at the most about 4% amino sugars and at the most about 15% desoxyribonucleic acids.

DETAILED DESCRIPTION OF THE INVENTION

In principle, any Gram-positive or Gram-negative bacterial strain or strains can be used as starting material or materials in the process according to the invention, such as Escherichia coil or one or more of the bacterial strains described in the above-mentioned patent CH 633 188, namely, *Staphylococcus aureus,* strains I-049, I-050, I-051, I-052, I-053 and I-054, which have been assigned by the "Collection Nationale de Cultures de Microorganismes, Institut Pasteur" numbers I-1038 to I-1043 respectively; *Streptococcus viridans,* strains I-046, I-047 and I-048, which have been assigned by the "Collection Nationale de Cultures de Microorganismes, Institut Pasteur" numbers I-1035 to I-1037 respectively; *Neisseria catarrhalis* strain I-045, which has been assigned by the "Collection Nationale de Cultures de Microorganismes, Institut Pasteur" number I-1034; *Hemophilus influenzae* serotype b. For example, the process which is described hereafter uses an *Escherichia coli* strain, in particular the strain I-1147 deposited according to the Budapest Treaty on Oct. 3rd 1991 at the Collection Nationale de Cultures de Microorganismes, Institut Pasteur, 25 rue du Dr. Roux, 75724 PARIS CEDEX 15—FRANCE.

EXAMPLE

A. Preliminary steps

A primary inoculum is prepared from frozen bacteria which are revived by alternating growth in a liquid medium such as the "tryptic soya broth" and on a solid medium. The volume of the cultivation medium of the inoculum is increased progressively to 1 l, using a conventional cultivation medium and incubation at 37° C. under agitation.

The secondary inoculum thus prepared is introduced into a 20 l fermentation vessel containing 5 l of an appropriate conventional nutrient medium. The pH is adjusted and maintained at 7.0 for example with 5% ammonia and the temperature is kept at 37° C. The bacterial growth is carried out under controlled conditions of aeration (air) and agitation, to achieve a $pO_2$ in excess of 90% of saturation. The optical density is measured at 700 nm. At the end of the cultivation, the bacteria are heat inactivated by autoclaving (30 minutes at 120° C.) or by a flash pasteurization (90 seconds at 105° C.) and a sample is taken to check for the absence of viable germs.

The bacterial suspension is concentrated and residual cultivation medium which was not used is separated by centrifugation or preferably by tangential ultrafiltration, for example with an ultrafiltration system of the "FILTRON" type, using polysulfone cartridges. This ultrafiltration is carried out in two steps, the first one consisting of a 5- to 10-fold concentration (30 kD to 0.13 μm membranes) and the second one of a washing by diafiltration with physiological saline (3 to 15 volumes of washing solution).

The dry matter of the bacterial suspension is determined, which makes it possible to adjust the biomass of the preparation before subjecting it to the alkaline extraction. The final bacterial suspension is diluted in physiological saline and the final dry weight of the bacteria is adjusted between 2 and 20 g/l.

B. Alkaline extraction

For the actual alkaline extraction, the NaOH concentration of the bacterial suspension is adjusted generally between 0.01 and 1%, here at 0.1%.

The extraction is carried out generally between 30° and 45° C. under agitation, here at approximately 37° C. Samples are taken in the course of time for analytical purposes. These analyses include the measuring of the pH, the determination of proteins and of lipopolysaccharides. The bacteria used for obtaining batches I and II were concentrated and washed (step A) using a 30 kD cartridge whereas a 1000 kD cartridge was used in the case of batch III. In the present examples, the alkaline extraction lasted a little less than two days. The results concerning the three batches (I, II and III) obtained with the above-mentioned *Escherichia coli* strain are given in table 1.

TABLE 1

| Batch | Dry matter (g/l) | Time | pH | Proteins* (mg/l) | LPS** (mg/l) |
|---|---|---|---|---|---|
| I | 7.4 | 0 min | 7.0 | 220 | >100 |
| | | 5 min | 12.3 | 910 | 100 |
| | | 22 hr | 12.3 | 1530 | 8.0 |
| | | 46 hr | 12.3 | 1850 | 1.0 |
| II | 7.4 | 0 min | 7.0 | 250 | >100 |
| | | 5 min | 12.4 | 870 | 100 |
| | | 22 hr | 12.4 | 1580 | 10 |
| | | 46 hr | 12.3 | 1990 | 3.3 |
| III | 7.0 | 0 min | 7.0 | 60 | >100 |
| | | 5 min | 12.4 | 710 | 100 |
| | | 22 hr | 12.4 | 1260 | 10 |
| | | 46 hr | 12.4 | 1640 | 1.0 |

*Determination of proteins according to the Bradford method
Reference: Bovine serum albumin (BSA)
Determination of PS according to the LAL method
Reference : LPS of *Escherichia coli* 0111:B4

This monitoring further enables those versed in the art to determine the appropriate duration for the alkaline extraction process depending on the final use, the type of bacteria treated, as well as the pH and temperature conditions. This duration is generally comprised between several hours and about one week.

Concerning the pH, it should be reminded that one of the characteristics of the process according to the invention is its stability, and the pH is maintained between 11 and 13, for example between 12.0 and 12.5, with a decrease during the extraction process not exceeding 0.4. In the present example, the pH was of 12.3–12.4 with a maximum variation of 0.1 during the extraction.

An important additional advantage of the process according to the invention is apparent from the results shown in table 1: one can actually see that the lipopolysaccharide content in the protein extract obtained is noticeably reduced.

At the end of the extraction and before the purification of the protein extract, a microscopic control of the bacteria after a Gram coloration is carried out in order to verify that the apparent structures of the bacteria are intact.

C. Purification of the protein extract.

The protein extract, obtained by the process described under (B) is subjected to an ultrafiltration step; specifically, it is subjected to a 5- to 10-fold concentration by ultrafiltration (1000 kD) and the active principle is extracted by diafiltration, using water for example. The protein extract is finally concentrated by ultrafiltration (10 kD).

In order to eliminate the major part of the endotoxins, more particularly of the LPS, the protein extract is subjected to a phase transfer procedure using a non ionic surfactant. For example, this procedure can be carried out in the presence of "Triton X-114" 7%, by heating to approximately 60° C. under agitation during about 20 minutes. After phase separation, the lower phase (Triton+LPS) is discarded. The upper aqueous phase containing the protein extract is collected and the pH is adjusted to 7.

This aqueous phase is subjected to an anion exchange chromatography for further reducing the LPS content and eliminating the non ionic surfactant. One can use in this chromatography a DEAE-Sepharose gel for example. Specifically, the aqueous phase containing the protein extract is first adsorbed on the anion exchange resin, and then the molecules which are not retained are eliminated and a washing at low pH eliminates the impurities. After equilibration of the gel at neutral pH, the protein extract is eluted by increasing the ionic strength, and the eluate is concentrated by ultrafiltration and washed by diafiltration using water. The protein extract thus purified is subjected to a sterile filtration and, if desired, lyophilized in a manner known per se.

Biochemical analyses and immunopharmacological tests were carried out on the lyophilized product. The determination of the amino acids racemized during the alkaline extraction was carried out according to Nimura N. and Kinoshita T., J. Chromatography, 352, 169–177, 1986. The different racemizations found in the protein extracts (batches I, II and III) are given by way of example in table 2 and are expressed as the percentage of D configuration.

TABLE 2

| Parameters | Racemized amino acids | | |
|---|---|---|---|
| | Percentage of D configuration | | |
| Batches | I | II | III |
| Racemized amino acids: | | | |
| Aspartic acid | 18 | 18 | 20 |
| Serine | 33 | 35 | 39 |
| Arginine | 8 | 10 | 12 |

Were not racemized: alanine, tyrosine, valine, phenylalanine and leucine
Were not detected: glutamic acid, threonine, proline, methionine, isoleucine, cysteine, lysine, histidine and tryptophan.
The analytical results are given in table 3.

TABLE 3

| Parameters | Components of the lyophilized product. | | |
|---|---|---|---|
| | Percentage of lyophilized product | | |
| Batches | I | II | III |
| Protein content: | | | |

TABLE 3-continued

Components of the lyophilized product.

| Parameters | Percentage of lyophilized product | | |
|---|---|---|---|
| Batches | I | II | III |
| Proteins (Bradford) | 69.2 | 70.14 | 63.1 |
| Protein amino acids: | | | |
| Asparagine & aspartic acid | 7.3 | 7.6 | 7.1 |
| Glutamine & glutamic acid | 9.6 | 9.5 | 8.9 |
| Serine | 2.6 | 2.4 | 2.2 |
| Threonine | 2.9 | 3.2 | 2.3 |
| Glycine | 3.8 | 3.9 | 3.3 |
| Alanine | 5.9 | 5.6 | 5.6 |
| Arginine | 4.8 | 4.6 | 5.3 |
| Proline | 2.5 | 2.4 | 2.5 |
| Valine | 4.9 | 5.0 | 4.4 |
| Methionine | 3.1 | 4.0 | 3.4 |
| Isoleucine | 4.1 | 4.0 | 3.5 |
| Leucine | 6.3 | 6.3 | 5.9 |
| Phenylalanine | 3.3 | 3.3 | 3.3 |
| Cystine | ND | ND | ND |
| Lysine | 5.0 | 4.9 | 4.7 |
| Histidine | 1.6 | 1.9 | 1.9 |
| Tyrosine | 3.9 | 4.0 | 3.9 |
| Total | 71.7 | 72.6 | 68.1 |
| Fractions linked to proteins: | | | |
| Fatty acids | 0.9 | 0.9 | 1.0 |
| Glucides | 3.9 | 3.6 | 4.7 |
| Amino sugars | 1.8 | 1.5 | 2.8 |
| Others: | | | |
| Lipopolysaccharides (LPS) | $6.1 \times 10^{-4}$ | $8.4 \times 10^{-4}$ | $2.5 \times 10^{-4}$ |
| Desoxyribonucleic acids (DNA) | 9.5 | 6.1 | 4.5 |
| Free amino acids | ND | ND | ND |
| Water | 4.8 | 4.9 | 4.8 |
| Elementary analyses | | | |
| Ashes | 6.0 | 7.5 | 7.2 |
| Carbon | 47.1 | 47.0 | 46.3 |
| Hydrogen | 6.7 | 6.7 | 6.6 |
| Nitrogen | 13.6 | 14.0 | 13.6 |
| Sulfur | 1.3 | 1.4 | 1.8 |

ND = Not detected

Immunopharmacological Properties

It was clearly demonstrated, in particular by in vitro and in vivo tests on model animals, that the protein extract according to the invention has immunomodulator properties and an antineoplastic activity.

1. In vitro immunological tests

The in vitro immunological tests were carried out on macrophages derived from bone marrow and on lymphocytes from the spleen, Peyer's patches or mesenteric glands, of mice C57BL/6.

Macrophage models: The protein extract stimulates macrophages in their capacity to activate the oxidative metabolization of glucose through the pentose phosphate pathway and activates the production of nitrogen metabolites (nitrite test). The secretion of TNF and also the production of prostaglandins (PGE$_2$) in macrophages is stimulated by the protein extract.

The nitrite test, given by way of example, was carried out according to Marletta M. A., Biochemistry, 27, 8706-8711, 1988. The macrophages derived from bone marrow are cultured on microplates (70,000 macrophages per well) in the presence of different concentrations of the protein extract (0.1 to 50 μg of extract/ml) or of E. coli lipopolysaccharides used as positive controls (0.0004 to 0.2 μg LPS/ml). The production of NO$_2^-$ in the supernatants of the macrophage cultures is determined using Griess' reagent according to Mauël J. and col., Int. J. Immunopharmac., 11, 637-645, 1989.

TABLE 4

Results of the nitrite test

| μg of extract/ml | nmoles NO$_2^-$/ml | μg LPS/ml | nmoles NO$_2^-$ |
|---|---|---|---|
| 0 | <0.02 | 0 | <0.02 |
| 0.1 | 0.9 ± 0.1 | 0.0004 | 0.1 ± 0.1 |
| 0.39 | 4.1 ± 0.1 | 0.0016 | 0.3 ± 0.1 |
| 1.56 | 7.7 ± 0.2 | 0.0063 | 4.2 ± 0.1 |
| 6.25 | 10.8 ± 0.2 | 0.025 | 6.5 ± 0.4 |
| 25.0 | 13.1 ± 0.8 | 0.1 | 7.1 ± 1.0 |
| 50.0 | 15.1 ± 0.3 | 0.2 | 8.3 ± 0.2 |

The results at different concentrations of the products tested are shown in table 4 in nmoles of NO$_2^-$/ml of cellular supernatant as a function of the concentration of the extract or of LPS. The protein extract induces a strong production of NO$_2^-$.

Lymphocytic models: Lymphocytes from the spleen, Peyer's patches or mesenteric glands are cultured on microplates ($5 \times 10^5$ cells per well) under standard cultivation conditions in the presence of different concentrations of the protein extract (1 to 100 μg extract/ml) or of different concentrations of E. coli polysaccharide in the positive controls (1 to 100 μg of LPS/ml). The cell proliferation induced by the products is determined by the level of incorporation of tritiated thymidine into the DNA of the cells, according to Louis J. and col., Eur. J. Immunol., 9, 841-847, 1979. The amplitude of the stimulation of the lymphocytes by the protein extract is compared, at the same concentration, to that of the positive control for the 3 sources of lymphocytes. The protein extract is active already at 1 μg extract/ml and exhibits a maximum of activity between 30 and 100 μg of extract/ml.

2. In vivo immunological test.

The antineoplastic activity of the protein extract was demonstrated in vivo using a model peritoneal carcinoma induced in rats BD IX.

Cells used: Pro b cells were cloned from a culture of K12 cells, which were isolated from a DHD tumor induced by dimethylhydrazine in a consanguineous rat BD IX, according to Martin F. and col., Int. J. Cancer, 32, 623-627, 1983.

Induction of peritoneal carcinomas: Pro b cells, administered by intraperitoneal injection to syngenic rats ($10^6$ cells/rat) give rise after about ten days to numerous solid nodules which appear in the epiploon or in the mesenterium at the milky spots, and then invade progressively the peritoneal cavity, as was described by Lagadec P. and col., Invasion and Metastasis, 7, 83-95, 1987. A hemorrhagic ascites appears 4 to 5 weeks later and all the rats die within 8 to 12 weeks.

Induction of pulmonary metastases: The injection of $7 \times 10^6$ Pro b cells into the femoral vein causes the invasion of all the pulmonary lobes by metastases and all the rats die within 6 to 10 weeks.

Treatment of peritoneal and pulmonary carcinomas: The immunotherapy starts 14 days after the injection of the tumor cells, when the carcinomas become visible to the eye. The treatment consists in administering the protein extract by intraperitoneal injection at 10 mg per kg of body weight. The rats receive a total of 5 injections, at intervals of 3 to 5 days. Each experiment includes a control group and a treated group of 10 (or 12) rats, which all carry a number.

Results: The rats are sacrificed 6 weeks after the injection of the cells and an autopsy is practised. The volume of the peritoneal carcinomas is evaluated blindly and the rats are ranked by increasing carcinomatosis. A scale for the carcinomatosis is established, based on the number and on the size of the nodules which are observed. The volume of the hemorrhagic ascites is determined by double weighing. The classification of pulmonary metastases was carried out after a microscopic examination of the lungs of the rats, which were classified either as having metastases or as being free of metastases.

The results obtained show that in eight experiments performed on 82 treated rats, 41 rats did not exhibit any nodule at the autopsy (40 to 60% of the rats per experiment); in the other rats, the growth of the nodules was substantially inhibited. Further, 78 of the 82 treated rats had no ascites. All the non treated rats had tumors and hemorrhagic ascites. These results are confirmed by those obtained in a survival experiment: of 10 rats treated with the protein extract, 3 rats survived 10, 18 and 27 months after the injection of cancer cells and showed no tumor at the autopsy. All the rats of the control group died from their tumor 3 months after the injection of the cells.

Further, the results obtained in 2 experiments on the growth of pulmonary metastases made it possible to demonstrate that the protein extract has a systemic effect. Actually, of 20 rats treated by intraperitoneal injection, 13 exhibited a complete inhibition of the growth of the pulmonary metastases. The antineoplastic effect of the protein extract is obtained on metastases induced by the cancerous cells of the colon and also by dissociated tumors. No indication of toxicity was found during the treatment.

3. Acute toxicity

The toxicity of the protein extract is low. Single doses ranging up to 300 mg per kg, administered by intraperitoneal injection, are well tolerated by mice.

4. Administration

The administration of the protein extract is carried out by injection, preferably by intraperitoneal injection of the lyophilized product dissolved for example in physiological saline. Other dosage forms can also be envisaged, for example dosage forms designed for oral, rectal or topical administration.

We claim:

1. A modified bacterial protein-based extract comprising a mixture of extracted acidic bacterial polyanions having an isoelectric point of 2.5 to 5.5, and wherein the sum of amino acid constituents represents at least 50% of said extract, said extract having been prepared by carrying out an alkaline extraction of a bacterial suspension in the presence of a diluted aqueous source of hydroxyl ions at a stable pH ranging between 11 and 13, followed by a purification of the extract, wherein said bacterial suspension comprises at least one bacterial strain selected from the group consisting of *Staphylococcus aureus,* strains I-049, I-050, I-051, I-052, I-053 and I-054; *Streptococcus viridans,* strains I-046, I-047 and I-048; *Neisseria catarrhalis* strain I-045; *Hemophilus influenzae* serotype b NCTC 8467; *Diplococcus pneumoniae* serotypes 1, 2, 3 and 47, NCTC 7465, 7466, 7978 and 10319, respectively; *Klebsiella pneumoniae* strains NCTC 204 and 5056; *Klebsiella ozaenae* NCTC 5050; *Streptococcus pyogenes* serogroup A NCTC 8191; *Neisseria catarrhalis* strains NCTC 3622 and 3625, and *E. coli* I-1147.

2. The modified bacterial protein-based extract according to claim 1, wherein the sum of amino acid constituents ranges from 55 to 85% of said extract, said extract including a lipopolysaccharide content of less than about $2 \times 10^{-3}\%$, at most about 2% of free amino acids, at most about 8% of glucides, at most about 4% of amino sugars, and at most about 15% of desoxyribonucleic acid, and wherein among the protein amino acids, of which some are racemized, acid groups including aspartic acid and glutamic acid groups predominate.

3. The modified bacterial protein-based extract according to claim 2, wherein the racemized amino acids are at least serine having 25 to 45% D configuration, aspartic acid 10 to 30%, and arginine 3 to 20%.

4. A process for the preparation of a modified bacterial protein-based extract which comprises cultivating bacteria in a liquid medium, suspending said bacteria in an aqueous medium so as to obtain a bacterial suspension, carrying out an alkaline extraction on said bacterial suspension, and thereafter a purification so as to obtain said modified bacterial protein-based extract, said alkaline extraction being carried out in the presence of a diluted aqueous source of OH ions at a stable pH ranging between 11 and 13, and a decrease in pH during said extract not exceeding 0.4, wherein the cultivated bacteria comprise at least one bacterial strain selected from the group consisting of *Staphylococcus aureus,* strains I-049, I-050, I-051, I-052, I-053 and I-054; *Streptococcus viridans,* strains I-046, I-047 and I-048; *Neisseria catarrhalis* strain I-045; *Hemophilus influenzae* serotype b NCTC 8467; *Diplococcus pneumoniae* serotypes 1, 2, 3 and 47, NCTC 7465, 7466, 7978 and 10319, respectively; *Klebsiella pneumoniae* strains NCTC 204 and 5056; *Klebsiella ozaenae* NCTC 5050; *Streptococcus pyogenes* serogroup A NCTC 8191; *Neisseria catarrhalis* strains NCTC 3622 and 3625, and *E. coli* I-1147.

5. A process according to claim 4, wherein the source of OH ions is 0.01 to 1% NaOH, the pH ranges from 12.0 to 12.5, and the temperature is maintained between 30° and 45° C. during extraction for a period ranging from several hours to one week.

6. A process according to claim 5, wherein the cultivated bacteria is *Escherichia coli* I-1147.

7. A process according to claim 4, wherein after purification, the LPS content of the modified bacterial protein-based extract is less than $2 \times 10^{-3}\%$, said purification including one or several steps of ultrafiltration, treatment with a non-ionic surfactant, chromatography, sterile filtration, and lyophilization.

8. A pharmaceutical composition containing as the active ingredient a therapeutically acceptable amount of the modified bacterial protein-based extract according to claim 1.

9. A pharmaceutical composition according to claim 8, prepared in an injectable form, or in a dosage form for oral, rectal or topical administration.

* * * * *